US012697071B2

(12) United States Patent　　　(10) Patent No.:　US 12,697,071 B2
Billings et al.　　　　　　　　　　 (45) Date of Patent:　　　　Aug. 4, 2026

(54) DEEP LEARNING LYME DISEASE DIAGNOSIS

(71) Applicant: THE JOHNS HOPKINS UNIVERSITY, Baltimore, MD (US)

(72) Inventors: Seth D. Billings, Pellston, MI (US); Philippe M. Burlina, Rockville, MD (US); Neil J. Joshi, Laurel, MD (US); John N. Aucott, Lutherville, MD (US); Elise Ng, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 901 days.

(21) Appl. No.: 17/278,377

(22) PCT Filed: Sep. 24, 2019

(86) PCT No.: PCT/US2019/052724
§ 371 (c)(1),
(2) Date: Mar. 22, 2021

(87) PCT Pub. No.: WO2020/068848
PCT Pub. Date: Apr. 2, 2020

(65) Prior Publication Data
US 2021/0345971 A1　　Nov. 11, 2021

Related U.S. Application Data

(60) Provisional application No. 62/735,351, filed on Sep. 24, 2018.

(51) Int. Cl.
*A61B 5/00*　　　　(2006.01)
*G06N 3/08*　　　　(2023.01)
(Continued)

(52) U.S. Cl.
CPC .......... *A61B 5/7267* (2013.01); *A61B 5/0077* (2013.01); *A61B 5/444* (2013.01);
(Continued)

(58) Field of Classification Search
CPC ..... A61B 5/7267; A61B 5/0077; A61B 5/444; G16H 50/20; G06N 3/08
See application file for complete search history.

(56) References Cited

U.S. PATENT DOCUMENTS

2004/0008867 A1　　1/2004　Fein et al.
2010/0069758 A1*　3/2010　Barnes ................... A61B 5/445
　　　　　　　　　　　　　　　　　　　　　600/476

(Continued)

OTHER PUBLICATIONS

International Search Report and Written Opinion in corresponding International Application No. PCT/US2019/052724 mailed on Jan. 9, 2020, 6 pages.
(Continued)

*Primary Examiner* — Daniel L Cerioni
(74) *Attorney, Agent, or Firm* — MH2 Technology Law Group LLP

(57) ABSTRACT

Techniques for diagnosing Lyme disease are presented. The techniques may include obtaining a digital photo of a skin lesion, providing the digital photo to a deep learning convolutional neural network, such that an output diagnosis is provided. The deep learning convolutional neural network may be trained using a training corpus including a plurality of digital training images annotated according to one of a plurality of training image diagnoses, where the plurality of training image diagnoses include at least one Lyme disease type, normal skin, and at least one non-Lyme skin lesion type, and where the plurality of digital training images include multiple digital photographs publicly available on the internet. The techniques can include outputting the output diagnosis.

6 Claims, 5 Drawing Sheets

(51) Int. Cl.
  *G06T 7/00* (2017.01)
  *G16H 50/20* (2018.01)
(52) U.S. Cl.
  CPC .......... *A61B 5/6898* (2013.01); *A61B 5/7282*
      (2013.01); *G06N 3/08* (2013.01); *G06T*
      *7/0014* (2013.01); *G16H 50/20* (2018.01);
      *A61B 2576/02* (2013.01); *G06T 2207/20081*
      (2013.01); *G06T 2207/20084* (2013.01); *G06T*
      *2207/30088* (2013.01); *G06T 2207/30096*
                                          (2013.01)

(56) References Cited

U.S. PATENT DOCUMENTS

| | | | |
|---|---|---|---|
| 2014/0330335 A1 | 11/2014 | Errico et al. | |
| 2016/0305956 A1* | 10/2016 | Aucott | A61K 31/65 |
| 2018/0299445 A1* | 10/2018 | Shuber | G01N 33/574 |
| 2019/0079084 A1* | 3/2019 | Gordon | G01N 33/5438 |
| 2019/0392953 A1* | 12/2019 | Steuer | G16H 40/67 |
| 2021/0124995 A1* | 4/2021 | Mas Montserrat | G06F 16/55 |

OTHER PUBLICATIONS

International Preliminary Report on Patentability in corresponding Application No. PCT/US2019/052724 mailed on Mar. 23, 2021, 5 pages.

Goodfellow, I., "Deep Learning," Healthcare Informatics Research, The MIT Press, Cambridge, MA., Oct. 2016, pp. 351-354, vol. 22, No. 4.

Lecun, Y., "Deep learning," HAL open science, Nature, 2015, pp. 436-444, 521, 7553.

Girshick, R., "Rich feature hierarchies for accurate object detection and semantic segmentation," In: IEEE Computer Vision and Pattern Recognition, 2014, 8 pages.

Krizhevsky, A., "ImageNet Classification with Deep Convolutional Neural Networks," In: Advances in Neural Information Processing Systems, Communications of the ACM, Jun. 2017, pp. 84-90, vol. 60, No. 6.

Simonyan, K., "Very Deep Convolutional Networks for Large-Scale Image Recognition," arXiv:1409.1556v6 Apr. 10, 2015, 14 pages.

Szegedy, C., "Going Deeper with Convolutions," In: IEEE Computer Vision and Pattern Recognition (2015), 9 pages.

Landis, J.R., "The Measurement of Observer Agreement for Categorical Data," Biometrics, Mar. 1977, pp. 159-174, vol. 33, No. 1.

He, K., "Deep Residual Learning for Image Recognition," In: IEEE Computer Vision and Pattern Recognition, 2016, pp. 770-778.

Bhate, C., "Lyme disease. Part I. Advances and perspectives," J. Am. Acad. Dermatol. Apr. 2011, pp. 619-636, 64.

Bhate, C., "Lyme disease. Part II. Advances and perspectives," J. Am. Acad. Dermatol. Apr. 2011, pp. 639-653, 64.

Shapiro, E., "Lyme Disease," The New England Journal of Medicine, May 1, 2014, pp. 1724-1731, vol. 370, No. 18.

Esteva, A., "Dermatologist-level classification of skin cancer with deep neural networks," Nature, Feb. 2, 2017, pp. 115-118, vol. 542, No. 7639.

Tibbles, C.D., "Does This Patient Have Erythema Migrans?" JAMA, Jun. 20, 2007, pp. 1159-1160, vol. 298, No. 23.

Mazori, D.R., "Vesicular Erythema migrans: an atypical and easily misdiagnosed form of Lyme disease," Dermatology Online Journal, Aug. 2015, 6 pages, vol. 21, No. 8.

Aucott, J.N., "Bull's-Eye and Nontarget Skin Lesions of Lyme Disease: An Internet Survey of Identification of Erythema Migrans," Dermatology Research and Practice, 2012, 6 pages, vol. 2012, Article ID 451727.

Cuk, E., "Supervised Visual System for Recognition of Erythema Migrans, an Early Skin Manifestation of Lyme Borreliosis," Strojniki vestnik-J. Mech. Eng. 2014, pp. 115-123, vol. 60, No. 2.

Smith, R.P., "Clinical Characterization And Treatment Outcomes Of Early Lyme Disease In Patients With Microbiologically Confirmed Erythema Migrans," Ann. Inter. Med. 2002, pp. 421-428, vol. 136.

Kankanahalli, S., "Automated Classification Of Severity Of Age-Related Macular Degeneration From Fundus Photographs," Invest. Ophthalmol. Vis. Sci., Mar. 2012, pp. 1789-1796, vol. 54, No. 3.

Burlina, P., "Comparing Humans And Deep Learning Performance For Grading Amd: A Study In Using Universal Deep Features And Transfer Learning For Automated AMD Analysis, "Comput. Biol. Med., Mar. 1, 2017, pp. 80-86, vol. 82.

Burlina, P., "Automated Grading Of Age-Related Macular Degeneration From Color Fundus Images Using Deep Convolutional Neural Networks," JAMA Ophthalmol. 2017, pp. 1170-1176, vol. 135, No. 11.

Kuehn BM. "Cdc estimates 300,000 US cases of Lyme disease annually," JAMA, Sep. 18, 2013, p. 1110, vol. 310, No. 11.

Hinckley AF, "Lyme Disease Testing By Large Commercial Laboratories In The United States," Clin Infect Dis. May 30, 2014, pp. 676-681, vol. 59, No. 5.

Stanek, G, "Lyme borreliosis," The Lancet, Seminar, Sep. 7, 2011, pp. 461-473, vol. 379, No. 9814.

Nadelman, RB. "Erythema Migrans," Infect Dis Clin North Am., 2015, pp. 211-239, vol. 29, No. 2.

Steere, AC, "The Presenting Manifestations Of Lyme Disease And The Outcomes Of Treatment," N Engl J Med. Jun. 12, 2003, pp. 2472-2474, vol. 348, No. 24.

Wormser, GP, "The Clinical Assessment, Treatment, And Prevention Of Lyme Disease, Human Granulocytic Anaplasmosis, And Babesiosis: Clinical Practice Guidelines By The Infectious Diseases Society Of America," Clin Infect Dis. 2006, pp. 1089-1134 vol. 43, No. 9.

Centers for Disease Control and Prevention. Lyme Disease (Borrelia burgdorferi) 2017 Case Definition. http://wwwn. cdc.gov/nndss/conditions/lyme-disease/case-definition/2017/. Published 2017. Accessed Apr. 23, 2018.

Schriefer, ME. "Lyme Disease Diagnosis" Serology. Clin Lab Med. 2015, pp. 797-814, vol. 35, No. 4.

Mullegger, RR, Skin Manifestations of Lyme Borreliosis,: Diagnosis and Management. Am J Clin Dermatol. 2008, pp. 355-368, vol. 9, No. 6.

Lipsker, D, How accurate is a clinical diagnosis of erythema chronicum migrans? Prospective study comparing the diagnostic accuracy of general practitioners and dermatologist in an area where lyme borreliosis is endemic. Arch Dermatol. 2004;140(5):620-621.

Steere, AC, "Lyme borreliosis," Nat Rev Dis Primers. 2016, vol. 2, No. 16090.

Fujisawa, Y, "Deep learning-based, computer-aided classifier developed with a small dataset of clinical images surpasses board-certified dermatologists in skin tumor diagnosis," Br J Dermatol., 2019, pp. 373-381, vol. 180.

Fix, AD, "Racial Differences in Reported Lyme Disease Incidence," Am J Epidemiol. 2000, pp. 756-759, vol. 152, vol. 8.

Adamson, AS, "Machine Learning and Health Care Disparities in Dermatology," JAMA Dermatology. 2018.

* cited by examiner

DEEP LEARNING LYME DISEASE DIAGNOSIS

RELATED APPLICATION

This application claims the benefit of, and priority to, U.S. Provisional Patent Application No. 62/735,351 filed on Sep. 24, 2018, which is hereby incorporated by reference in its entirety.

FIELD

This disclosure relates generally to Lyme disease and its diagnosis.

BACKGROUND

Lyme disease is the most common vector-borne disease in the United States, with over 300,000 new cases annually. *Borrelia burgdorferi* is the causative bacterial agent of Lyme disease, and it is transmitted through the bite of an infected tick into the skin of the affected individual. Infection progresses through three stages, advancing from skin-limited disease to disseminated disease affecting the nervous, cardiac, and rheumatologic systems. In the majority of cases, the initial skin infection is manifested by a round or oval red skin lesion called Erythema migrans, which is a direct result of bacterial infection of the skin and marks the first stage of Lyme disease. Treatment with oral antibiotics is highly effective in early, uncomplicated cases. Therefore, recognition of Erythema migrans is crucial to early diagnosis and treatment, and ultimately, prevention of potentially devastating long-term complications.

Erythema migrans typically occurs one to three weeks after the initial tick bite and expands centrifugally by as much as a centimeter per day. Classically, the lesion will also display central clearing as it expands, leading to the hallmark bull's-eye rash of Lyme disease. However, many individuals will not display this finding and the majority of individuals are unable to recall a tick bite, making early diagnosis challenging. Erythema migrans usually persists for weeks during which its visual recognition is the primary basis for the clinical diagnosis of early Lyme disease. Following this early period, untreated Erythema migrans usually disappears or progresses to disseminated disease through the spread of infection through the bloodstream.

Diagnosis of early Lyme disease is usually made based on clinical signs and symptoms and history of potential exposure to ticks, due to the lack of reliable serologic blood testing early in the disease course. Blood tests are insensitive during the early phase of infection and are not recommended because of the high false negative rate at the time of initial Erythema migrans presentation. Only 25 to 40% will have positive results during the acute phase of infection. Direct detection of bacteria in blood or biopsy samples can be performed, but are generally unavailable in non-research settings and not practical due to the time required for results.

SUMMARY

According to various embodiments, method of diagnosing Lyme disease is presented. The method includes obtaining a digital photo of a skin lesion; providing the digital photo to a deep learning convolutional neural network, such that an output diagnosis is provided, where the deep learning convolutional neural network is trained using a training corpus including a plurality of digital training images annotated according to one of a plurality of training image diagnoses, where the plurality of training image diagnoses include at least one Lyme disease type, normal skin, and at least one non-Lyme skin lesion type, and where the plurality of digital training images include multiple digital photographs publicly available on the internet; and outputting the output diagnosis.

Various optional features of the above embodiments include the following. The at least one non-Lyme skin lesion type may include herpes zoster. The at least one non-Lyme skin lesion type may include *Tinea corporis*. The obtaining may include obtaining by a smart phone camera. The providing may include providing to the smart phone, and the outputting may include outputting by the smart phone. The obtaining, the providing, and the outputting may include obtaining by, providing to, and outputting by an app executing on the smart phone. The multiple digital photographs publicly available on the internet may be obtained using a search engine and search terms including: Erythema migrans, lyme, and bullseye rash. The at least one Lyme disease type may include simple Erythema migrans and diffuse Erythema migrans. The multiple digital photographs publicly available on the internet may be obtained without patient consent. The obtaining, the providing, and the outputting may be performed by a server computer communicatively coupled to the internet.

According to various embodiments, a system for diagnosing Lyme disease is presented. The system includes at least one processor that executes instructions to perform operations including: obtaining a digital photo of a skin lesion; providing the digital photo to a deep learning convolutional neural network, such that an output diagnosis is provided, where the deep learning convolutional neural network is trained using a training corpus including a plurality of digital training images annotated according to one of a plurality of training image diagnoses, where the plurality of training image diagnoses include at least one Lyme disease type, normal skin, and at least one non-Lyme skin lesion type, and where the plurality of digital training images include multiple digital photographs publicly available on the internet; and outputting the output diagnosis.

Various optional features of the above embodiments include the following. The at least one non-Lyme skin lesion type may include herpes zoster. The at least one non-Lyme skin lesion type may include *Tinea corporis*. The obtaining may include obtaining by a smart phone camera. The providing may include providing to the smart phone, and the outputting may include outputting by the smart phone. The obtaining, the providing, and the outputting may include obtaining by, providing to, and outputting by an app executing on the smart phone. The multiple digital photographs publicly available on the internet are obtained using a search engine and search terms including: Erythema migrans, lyme, and bullseye rash. The at least one Lyme disease type may include simple Erythema migrans and diffuse Erythema migrans. The multiple digital photographs publicly available on the internet may be obtained without patient consent. The obtaining, the providing, and the outputting may be performed by a server computer communicatively coupled to the internet.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Embodiments can solve the problem of diagnosing, such as pre-screening, Lyme disease. In general, diagnosing Lyme disease is difficult due in part to the variability of its associated rash, Erythema migrans. Studies have shown that neither the public nor physicians can identify Erythema migrans with high accuracy, particularly when it lacks the classic bullseye appearance. However, suspicion of Lyme is a critical first step in prompting care-seeking behavior, which may lead to missed opportunities for early diagnosis and a time when Lyme disease is most easily treated and cured. Some embodiments provide computer-assisted diagnosis with sensitivity superior to that of the average observer. Embodiments may thus lead to faster and more accurate lesion identification and a decrease in incident misdiagnosis of early Lyme disease. Now that much of the general population has access to high-quality photography via smart phones, it has become increasingly common for patients to photograph their skin lesions. Some embodiments may be implemented as a smart phone app, which can pre-screen such "in the wild" photos and alert users to suspect Lyme disease. This may lead patients to care that they might not otherwise seek, which is expected to decrease missed early diagnoses, when Lyme is most treatable. These and other features and advantages are disclosed herein.

Figure 1:
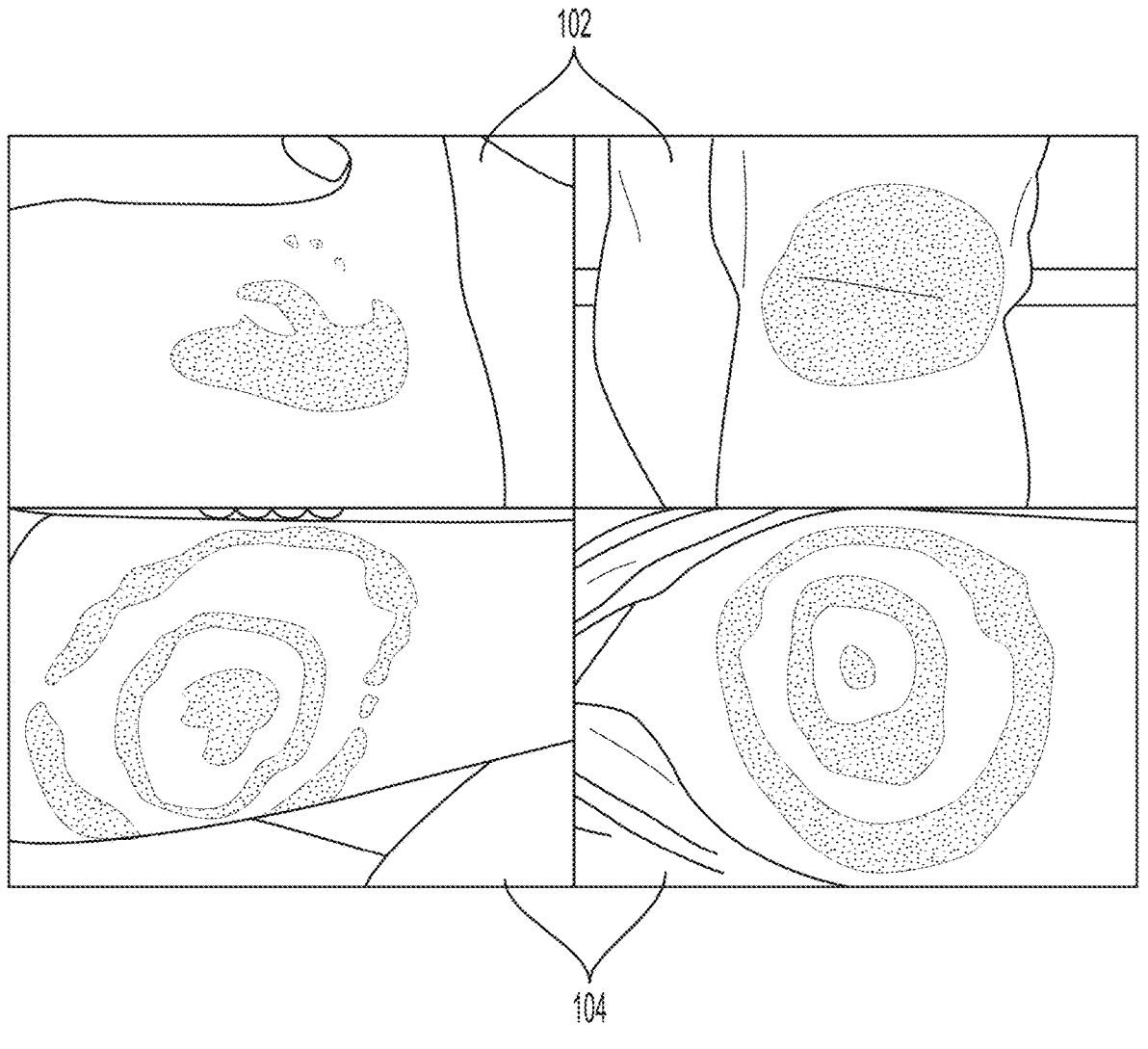
FIG. 1 depicts various presentations of Erythema migrans.

FIG. 1 depicts various presentations 102, 104 of an Erythema migrans (hereinafter, "EM") rash. The clinical diagnosis of early Lyme disease and EM is still a challenge. This is because EM may take on a variety of appearances besides the characteristic ring-within-a-ring, or bull's-eye rash presentation 104. The majority (80%) of EM lesions in the US lack the central clearing of the stereotypical bull's eye lesion and appear uniformly red or bluish red, as in atypical presentations 102. Thus, they are often mistaken for a spider bite or bruise. A small percentage (4-8%) of skin lesions have a small central blister, which may lead to the incorrect diagnosis of shingles (herpes zoster). Approximately 20% of patients have multiple skin lesions arising from the spread of infection through the bloodstream, which often have an atypical appearance. Atypical skin lesions are often misdiagnosed, which results in delayed diagnosis and treatment and increases risk of long-term complications.

Previous work has shown that the general population does not correctly identify EM skin lesions that lack the classic bull's-eye appearance and misidentify this condition approximately 80% of the time. As 80% of skin lesions do not have the bull's eye appearance, this means that approximately 60% of all EM lesions may be misdiagnosed by patients (80% of 80%). Machine-based prescreening of skin lesions associated with Lyme disease has the potential to identify a high percentage of both typical and atypical lesions, thereby decreasing the incidence of misdiagnosis of early Lyme disease.

Prior to 2012 and the demonstration of significant improvement in object recognition performance on ImageNet via the use of DCNNs (e.g., AlexNet), object classification in computer vision was largely based on applying traditional classifiers to hand-engineered image features. DCNNs have replaced these approaches for both computer vision and medical imaging tasks, and recently, they have been successfully used for performing a number of medical imaging diagnostics, including identifying skin cancer. To the best of our knowledge, however, Lyme disease detection from skin lesions has only been addressed thus far using classical machine learning approaches.

Some embodiments expand on prior state of the art with the following novel and salient contributions. Some embodiments utilize a novel, carefully clinician-annotated dataset, which includes images with several types of fine-grained annotations for skin lesions, mostly focused on EM, but also including other conf user lesions and clear/unaffected cases. Some embodiments utilize a DCNN approach that achieves a significant performance improvement over prior state of the art and demonstrates substantial agreement with human clinician annotations. Embodiments can potentially be used by others for fine tuning and transfer learning for addressing classification of other types of skin affects, including skin cancer lesions.

Embodiments may be implemented as solving a two-class classification problem, classifying images into patients that have EM (Lyme disease) vs. individuals that have no skin lesions or another skin condition, including confounding skin lesions. The main confusers that are considered in this second class include cases of herpes zoster (HZ), also known as shingles. HZ may be used as the principal conf user, with the rationale some embodiments may be used as a pre-screening tool, possibly implemented as a smartphone application, that could help individuals self-identify and screen lesions suspicious for Lyme disease. An acute onset rash, such as HZ, might prompt an individual to suspect Lyme disease and seek medical attention. Such embodiments may be targeted towards such individuals for whom such a tool would provide a means of disambiguation.

Figure 2:
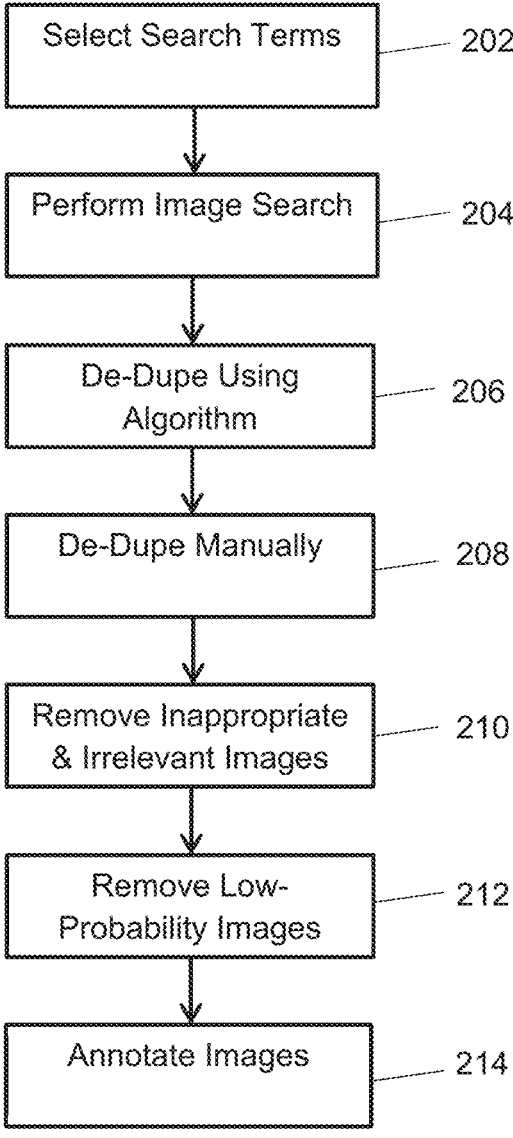
FIG. 2 is a flow diagram for a method of obtaining a training corpus of images according to various embodiments.

FIG. 2 is a flow diagram for a method 200 of obtaining a training corpus of images according to various embodiments. Because an annotated, and publicly available dataset for the study of machine pre-screening of Lyme disease and EM is not available, and because there is a paucity of clinical images having the associated consent and approval required for their usage, some embodiments may create and utilize an image dataset using publicly available images extracted from the web. Such online images of skin lesions may include those of EM, herpes zoster, other non-Lyme skin lesions, and normal skin. Such images may be mined from online sources. Note that obtaining patient consent is not required in order to use publicly-available photos on the web.

Thus, at 202, search terms are selected. Search terms may include any, or a combination, of "Erythema migrans", "lyme", "bullseye rash", "leg", "face", and "african american".

At 204, an image search is performed using the search terms selected at 202. Such an image search may be performed using a publicly-available search engine, such as GOOGLE. The image search results in obtaining an initial set of images.

At 206, the initial set of images may undergo automated de-duping to remove any duplicate images. Any known machine-based removal of full or near duplicates may be utilized.

At 208, the resulting set of images may be assessed by a human to de-dupe, so as to remove duplicate or near-duplicate images.

At 210, the resulting set of images may undergo human-performed removal of inappropriate and/or irrelevant images.

At 212, clinicians may carefully annotate each image in the resulting set of images based on the visual appearance and on the estimated size of the skin lesions. Clinicians may do a whole image classification first using a high level labeling of the pathology. This may be followed by a fine grained annotation that included the type of specific EM that was present (e.g. simple vs. diffuse).

At 214, a subset of the resulting set of images may be selected to include images with moderate to high probability of depicting EM or herpes zoster (and other confounding skin lesions). Note that certain characteristics inherent to online images, such as variability in viewpoint/angle, lighting, and photo resolution, may make the annotation of 212 difficult. At annotation time, the inability to verify the skin lesion through inspection at different angles or magnification in order to estimate the size of the skin lesion in some cases may be an issue. However, images for which there is significant ambiguity or uncertainty in diagnosis due to these factors may be excluded at 214. For example, images with a low probability of EM or HZ diagnosis may be excluded from the dataset. Thus, a two-class partitioning of images into affected and unaffected classes may be accomplished.

Note that additional images may be added to the images obtained using a web search. For example, some embodiments may include a previously validated set of clinical EM images. According to an experimental embodiment, such a set of images was included together with over 1600 images retrieved from the web and processed according to method 200. The images in the added set were obtained from patients enrolled in a longitudinal cohort study of early Lyme disease. Research photographs were obtained at the time of initial Lyme disease diagnosis and study entry from participants after written consent was obtained. Participants were recruited from a Lyme-endemic area during known seasonal tick activity months, and all EM cases were verified by a physician at the time of diagnosis.

Figure 3:
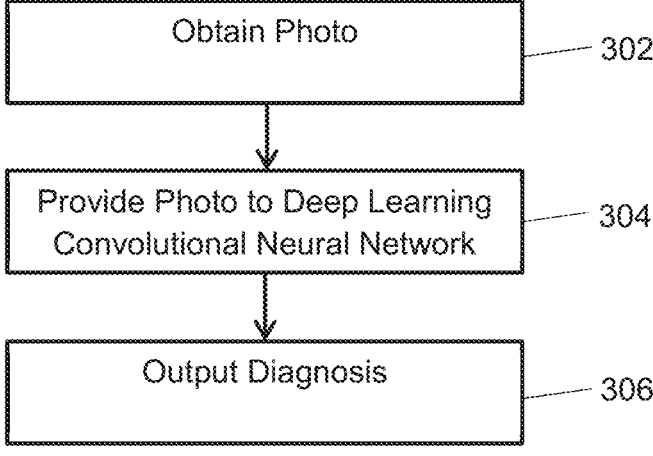
FIG. 3 is a flow diagram for a method of pre-screening for Lyme disease according to various embodiments.

FIG. 3 is a flow diagram for a method 300 of pre-screening for Lyme disease according to various embodiments. Method 300 may be implemented in a variety of systems. According to some embodiments, method 300 is implemented entirely by an app executing on a smart phone of a person. Alternately, method 300 may be partially implemented by a smart phone. Alternately, method 300 may be performed by any computer. Regardless as to the device that performs method 300, the trained deep learning convolutional neural network itself may be implemented at the user device or remotely. When implemented remotely, the user device may capture the photo per 300, provide the photo to the remote implementation of the neural network (e.g., over the internet) per 304, receive the results from the remote neural network, and provide the results to the user per 306. Thus, embodiments may be used by patients or by clinicians, and may be implemented for personal use, telemedicine, or in a point-of-care device, according to various embodiments.

At 302, method 300 obtains a photo of a skin lesion that might be EM. The photo may be captured by a smart phone of a patient or clinician. Alternately, or in addition, the photo may be captured by a camera in a clinical setting.

At 304, method 300 provides the photo to a trained deep learning convolutional neural network for classification. The photo may be provided to the neural network in a single device. For example, according to some embodiments, a smart phone may capture the photo and provide it to an executing app that includes the neural network within the smart phone. Alternately, a camera, whether in a smart phone or not, may capture the photo and then provide it to a remote server that implements the neural network. The neural network may have been trained using a training corpus of images obtained per method 200 as shown and described above in reference to FIG. 2.

A suitable example deep learning convolutional neural network as used in an experimental embodiment is described presently. The neural network takes a skin image as input and produces probabilities that the image belong to one of several specific classes of pathologies (e.g., EM vs. no EM) as output. Thus, the neural network was trained using 1695 images obtained per method 200, where 1387 such images were control images, depicting unaffected and confuser skin legions such as HZ, and where 308 such images were EM. The ResNet50 neural network architecture of He, K., et al., Deep residual learning for image recognition, IEEE Computer Vision and Pattern Recognition (2016) was used in the experimental embodiment. ResNet was originally conceived as a means of producing deeper networks and include specific design patterns such as bottleneck and skip connections that make the output of upstream layer directly available to downstream layers. The experimental embodiment used the Keras and TensorFlow frameworks. The experimental embodiment used transfer learning and fine-tuned the original ResNet50 weights using the skin classification problem addressed herein. The experimental embodiment used stochastic gradient descent with Nesterov momentum=0.9 for training, with initial learning rate set to 1 E-3. The training scheme used an early stopping approach, which terminates training after 10 epochs of no improvement of the validation accuracy. The experimental embodiment used a categorical cross entropy loss function. Dynamic learning rate scheduling was also used, in which the learning rate is multiplied by 0.5 when the training loss did not improve for 10 epochs. A batch size of 32 was used. Data augmentation was used and included horizontal flipping, blurring, sharpening, and changes to saturation, brightness, contrast, and color balance.

According to the experimental embodiment, the datasets were further subdivided into training and testing subsets. The experimental embodiment used a K-fold cross-validation method, with K=5, where four folds were employed for training and one fold was used for testing (with rotation of the folds for 5 runs). One training fold was further equally subdivided into two parts, with one used for validation and stopping conditions. In sum, the train/validation/test partition distribution for the experimental embodiment was 70%/10%20%, respectively.

At 306, method 300 may output a diagnosis based on the output of the neural network. For example, the output diagnosis may correspond to the highest probability category output by the neural network. The output may be performed in a variety of ways, e.g., displaying on a smart phone or computer monitor, emailing, texting, or providing to clinical management software.

A discussion of results of the above-described experimental embodiment follows.

The performance metrics used to evaluate the experimental embodiment include accuracy, F1, sensitivity, specificity, PPV (positive predicted value), NPV, (negative predicted value) and kappa score, which discounts chance agreement. Because any classifier trades off between sensitivity and specificity, to compare methods, ROC (receiver operating characteristic) curves were used, showing detection probability (sensitivity) vs. false alarm rate (100%–specificity) and AUC (area under curve) was computed.

Figure 4:
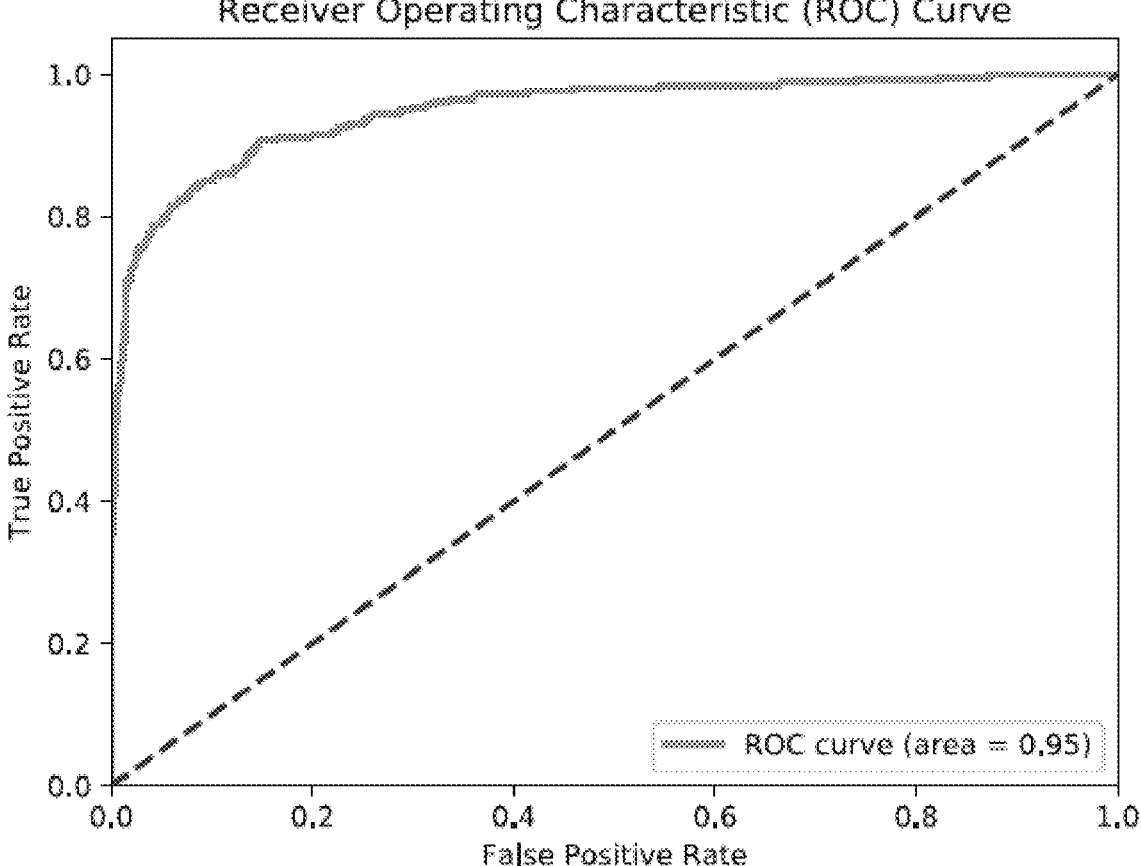
FIG. 4 depicts a receiver operation characteristics curve according to an experimental embodiment.

FIG. 4 depicts a receiver operation characteristics curve according to an experimental embodiment. As shown the area under the curve is 0.95, which is favorable. Further evaluation of the experimental embodiment are shown using five-fold cross validation. The Table below depicts the resulting metrics.

TABLE

| Metric | Value | Standard Deviation |
|---|---|---|
| Accuracy | 93.04 | 1.49 |
| Sensitivity/Recall | 75.66 | 7.28 |
| Specificity | 96.90 | 0.48 |
| PPV/Precision | 84.35 | 2.79 |
| NPV | 94.73 | 1.51 |
| Kappa | 0.7549 | 0.0586 |
| Positive Likelihood | 24.94 | 4.72 |
| Negative Likelihood | 0.25 | 0.076 |
| F1 Score | 0.7967 | 0.0502 |
| AUC | 0.9504 | 0.0156 |
| Confusion Matrix | \|1344 43\| | |
| | \|75 233\| | |

Results show promising accuracy of 93.04%. The ROC curve shows that one can operate with 90% sensitivity and above while having a specificity ranging in the 75% to 85% range, a tradeoff which suggests a potential for deployment as a pre-screener. Kappa score of 0.7549 also demonstrates substantial agreement with the human-annotated gold standard.

In sum, the experimental embodiment was able to substantially advance the state of the art in automated Lyme prescreening with deep learning neural network models that have significant promise for clinical deployment as pre-screeners. Such an application may prove to be of great utility given the challenges of diagnosing Lyme disease at an early stage when treatment is effective and can prevent the otherwise serious long-term complications associated with advanced Lyme disease. Based on these results, an application using deep learning neural networks is likely more sensitive than patient self-assessment and may even be more accurate than diagnosis by a general non-specialist physician, who would ordinarily serve as the screening gatekeeper for acute onset rashes such as EM. Given the frequent under-diagnosis of EM, the use of automated detection would be beneficial by increasing the number of patients who seek further medical assessment for EM rashes and minimizing the number of cases that go unevaluated and undiagnosed, with an expected positive effect on patient morbidity.

Note that data sets of images of EM rashes with annotation for research or teaching purposes are not currently widely available. Only one large study of EM rash characteristics in the United States from 2002 has been done. See Smith, R. P., Schoen, R. T., Rahn, D. W., *Clinical characterization and treatment outcomes of early Lyme disease in patients with microbiologically confirmed Erythema migrans*, Ann. Inter. Med. 136, 421-428 (2002). Physician review of images in that dataset reported an unexpected diversity in the appearance of EM lesions, with only 10% of lesions having the classic central clearing and ring-within-a-ring target appearance. The photos of EM lesions from that study had not been analyzed further using computerized approaches. To the inventors' knowledge, only one other study of computer-assisted detection of EM has been reported in the literature. See Čuk, E., et al., *Supervised visual system for recognition of Erythema migrans, an early skin manifestation of Lyme borreliosis*, Strojniški vestnik-J. Mech. Eng. 60, 115-123 (2014). That study used machine learning methods including boosting, SVM, naïve Bayes, and neural nets (but not deep learning) applied on hand-designed image features, and was tested with a smaller dataset of 143 EM rash images. Reported accuracies ranged from 69.23% to 80.42%. These results are a testimony to the difficulty in addressing the problem of how to discern between the varied presentations of the EM lesions. By comparison, the present results, performed on a much larger dataset, and images taken "in the wild", show notable enhancements in performance.

Figure 5:
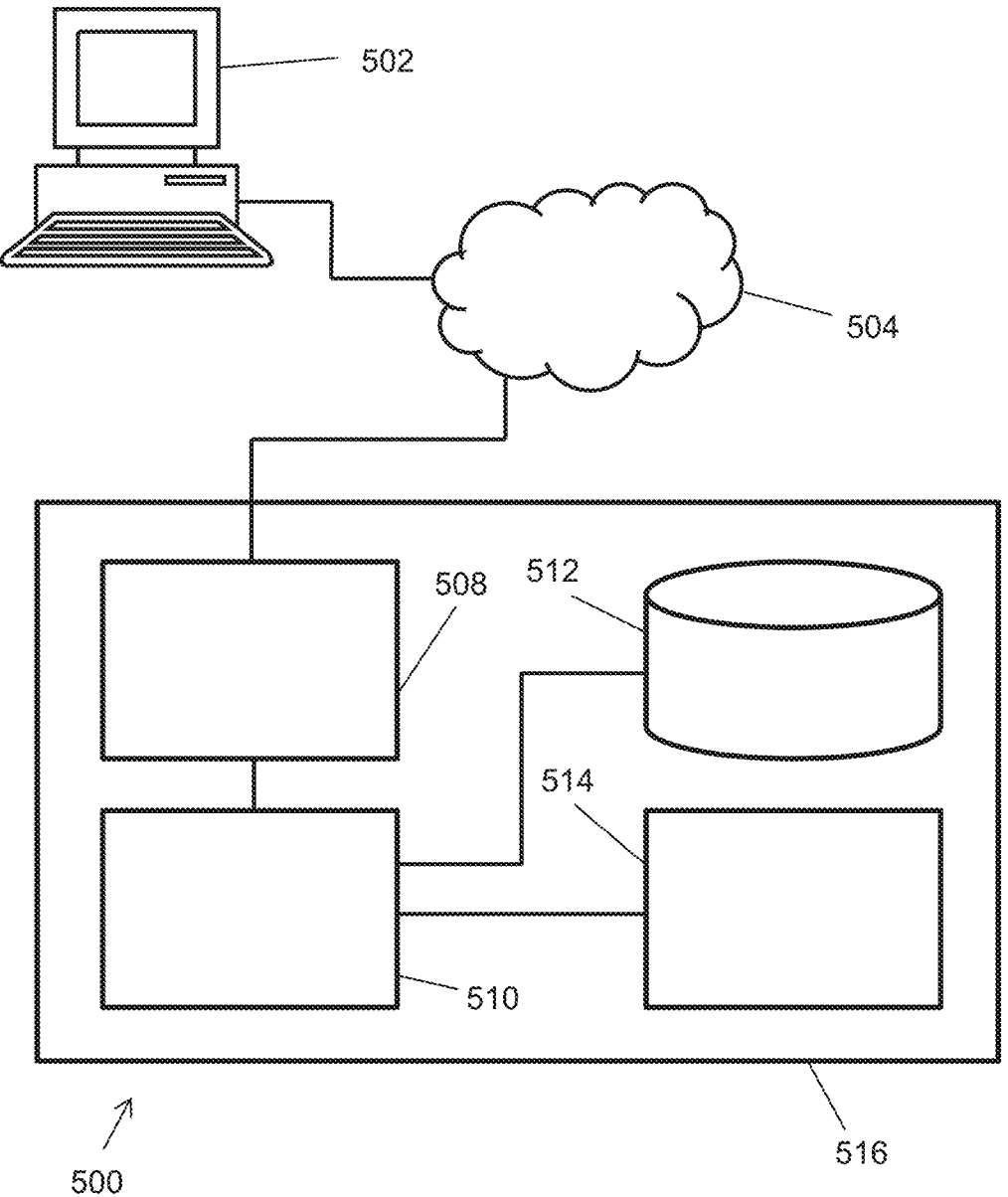
FIG. 5 is a schematic diagram of a system suitable for implementing various embodiments.

FIG. 5 is a schematic diagram of a system 500 suitable for implementing various embodiments. In particular, FIG. 5 illustrates various hardware, software, and other resources that may be used in implementations of a computer 500 system for implementing method 300. In embodiments as shown, computer system 500 includes server 516, which may include one or more processors 510 coupled to random access memory operating under control of or in conjunction with an operating system. The processors 510 in embodiments may be included in one or more servers, clusters, or other computers or hardware resources, or may be implemented using cloud-based resources. The operating system may be, for example, a distribution of the LINUX operating system, the UNIX operating system, or other open-source or proprietary operating system or platform. Processors 510 may communicate with data store 512, such as a database stored on a hard drive or drive array, to access or store program instructions other data.

Processors 510 may further communicate via a network interface 508, which in turn may communicate via the one or more networks 504, such as the Internet or other public or private networks, such that a photo may be received from client 502, or other device or service. According to various embodiments, client 502 may be a computer or a smart phone. A trained deep learning convolutional neural network as disclosed in detail herein may be implemented at computer system 516. Additionally, processors 510 may utilize network interface 508 to send a diagnosis or other data to a user via the one or more networks 504. Network interface 504 may include or be communicatively coupled to one or more servers.

Processors 510 may, in general, be programmed or configured to execute control logic and control operations to implement methods disclosed herein. Processors 510 may be further communicatively coupled (i.e., coupled by way of a communication channel) to co-processors 514. Co-processors 514 can be dedicated hardware and/or firmware components configured to execute the methods disclosed herein. Thus, the methods disclosed herein can be executed by processor 510 and/or co-processors 514.

Other configurations of computer system 506, associated network connections, and other hardware, software, and service resources are possible.

Certain embodiments can be performed using a computer program or set of programs. The computer programs can exist in a variety of forms both active and inactive. For example, the computer programs can exist as software program(s) comprised of program instructions in source code, object code, executable code or other formats, firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A system for diagnosing Lyme disease comprising at least one processor that executes instructions to perform operations comprising:

obtaining, by a smart phone camera, a digital photo of a skin lesion;

providing the digital photo to a deep learning convolutional neural network, whereby an output diagnosis is provided, wherein the output diagnosis is one of Lymes or not Lymes, wherein the deep learning convolutional neural network is trained using a training corpus comprising a plurality of digital training images annotated according to one of a plurality of training image diagnoses, wherein the plurality of training image diagnoses comprise at least one Lyme disease type diagnosis, normal skin, and at least one non-Lyme skin lesion type diagnosis, wherein the plurality of digital training images comprise a plurality of Lyme disease skin lesion training images depicting simple erythema migrans skin lesions and diffuse erythema migrans skin lesions, a plurality of normal skin training images, and a plurality of non-Lyme skin lesion training images depicting non-Lyme skin lesions, wherein the at least one non-Lyme skin lesion type comprises herpes zoster, wherein the at least one non-Lyme skin lesion type further comprises *Tinea corporis*, and wherein the plurality of digital training images comprise multiple digital photographs publicly available on the internet; and outputting in electronic format the output diagnosis.

2. The system of claim 1, wherein the providing comprises providing to the smart phone, and wherein the outputting comprises outputting by the smart phone.

3. The system of claim 2, wherein the obtaining, the providing, and the outputting comprise obtaining by, providing to, and outputting by an app executing on the smart phone.

4. The system of claim 1 wherein the multiple digital photographs publicly available on the internet are obtained using a search engine and search terms comprising: erythema migrans, lyme, and bullseye rash.

5. The system of claim 1, wherein the multiple digital photographs publicly available on the internet are obtained without patient consent.

6. The system of claim 1, wherein the obtaining, the providing, and the outputting are performed by a server computer communicatively coupled to the internet.

* * * * *